US008796230B2

United States Patent
Davies et al.

(10) Patent No.: US 8,796,230 B2
(45) Date of Patent: Aug. 5, 2014

(54) IVERMECTIN ANTAGONIZES ETHANOL INHIBITION IN P2X4 RECEPTORS

(75) Inventors: Daryl L. Davies, San Pedro, CA (US); Ronald L. Alkana, Seal Beach, CA (US); Liana Asatryan, Burbank, CA (US); Daya I. Perkins, Long Beach, CA (US); Maya S. Popova, Pasadena, CA (US)

(73) Assignee: University of Southern California, Los Angeles, CA (US)

( * ) Notice: Subject to any disclaimer, the term of this patent is extended or adjusted under 35 U.S.C. 154(b) by 227 days.

(21) Appl. No.: 13/011,162

(22) Filed: Jan. 21, 2011

(65) Prior Publication Data

US 2011/0201567 A1 Aug. 18, 2011

Related U.S. Application Data

(60) Provisional application No. 61/297,453, filed on Jan. 22, 2010.

(51) Int. Cl.
*A61K 31/7048* (2006.01)

(52) U.S. Cl.
USPC ............................................. 514/28; 536/7.1

(58) Field of Classification Search
USPC ............................................. 514/28; 536/7.1
See application file for complete search history.

(56) References Cited

PUBLICATIONS

Shu et al., Eur. J. Clin. Pharmacol., 2000, 56, p. 437-438.*
Entry for symptoms of alcoholism, MayoClinic.com, http://www.mayoclinic.com/health/alcoholism/DS00340/DSECTION=symptoms, accessed online on Feb. 19, 2013.*
Canga et al., The AAPS Journal, 2008, 10(1), p. 42-46.*
Abdo et al., Med. Oral Patol. Oral Cir. Bucal., 2006, 11(2), p. E130-E131.*
Asatryan, L. et al., "Implication of Purinergic System in Alcohol Use Disorders," Alcohol Clin Exp Res 35:584-594, 2011. PMID: 21223299.
Asatryan L. et al., "Ivermectin Antagonizes Ethanol Inhibition in P2X4 Receptors," J. Pharmacol. Exp. Ther. 334:720-8, 2010. PMID: 20543096.
Bortolato, M. et al., "Pharmacological insights into the role of P2X4 receptors in behavioral regulation: lessons from ivermectin," Int J Neuropsychopharmacology, Sep. 17, 2012:1-12. [Epub ahead of print] PMID:23174033.
Davies, D.L. et al. "Ethanol differentially affects ATP-gated P2X(3) and P2X(4) receptor subtypes expressed in *Xenopus oocytes*," Neuropharmacology 49, 243-253 (2005).
Davies, D.L. et al., "Recent advances in the discovery and preclinical testing of novel compounds for the prevention and/or treatment of alcohol use disorders," Alcohol Clin Exp Res, 37 (1): 8-15, 2013. PMID: 22671690.
Grant, B.F. et al, "The 12-month prevalence and trends in DSM-IV alcohol abuse and dependence: United States, 1991-1992 and 2001-2002," Drug Alcohol Depend 74, 223-234 (2004).
Harwood, H.J., "Updating estimates of the economic costs of alcohol abuse in the United States: Estimates, update methods, and data," Report prepared by the Lewin Group from the National Institute on Alcohol Abuse and Alcoholism. 2000, 17 pgs.
Heilig, M. et al., "Pharmacological treatment of alcohol dependence: target symptoms and target mechanisms," Pharmacol Ther. 111, 855-876 (2006).
Johnson, B.A. et al., "Topiramate for treating alcohol dependence: A randomized controlled trial," JAMA 298, 1641-1651 (2007).
Priel, A., et al. "Mechanism of Ivermectin facilitation of human P2X4 receptor channels," J. Gen. Physiol. 123, 281-293 (2004).
Yardley, M. et al., "Ivermectin Reduces Alcohol intake and preference in Mice," Neuropharmacology, 63: 190-201, 2012. PMID: 22465817.
Litten, R.Z. et al., "Medications development to treat alcohol dependence: a vision for the next decade," Addiction Biology 17, (2012), pp. 513-527.

* cited by examiner

*Primary Examiner* — Shaojia Anna Jiang
*Assistant Examiner* — Jonathan S Lau
(74) *Attorney, Agent, or Firm* — Brooks Kushman P.C.

(57) ABSTRACT

A method for reducing alcohol consumption in a subject includes a step of identifying a subject exhibiting at least one symptom of alcoholism and then administering a therapeutically effective amount of an Ivermectin analogue-containing composition to the subject. A method of screening Ivermectin analogues for reducing alcohol consumption is also provided.

17 Claims, 14 Drawing Sheets

A.

B.

C.

D.

A.

B.

C.

A.

B.

C.

IVERMECTIN ANTAGONIZES ETHANOL INHIBITION IN P2X4 RECEPTORS

CROSS-REFERENCE TO RELATED APPLICATIONS

This application claims the benefit of U.S. provisional Application No. 61/297,453 filed Jan. 22, 2010, the disclosure of which is incorporated in its entirety by reference herein.

STATEMENT REGARDING FEDERALLY SPONSORED RESEARCH OR DEVELOPMENT

The invention was made with Government support under Grant Nos. AA013922; AA013517; and AA017243. The Government has certain rights to the invention.

TECHNICAL FIELD

In at least one aspect, the present invention provides a method of alleviating at least one symptom of alcoholism.

BACKGROUND OF THE INVENTION

ATP-gated P2X receptors (P2XRs) are a superfamily of ligand-gated ion channels (LGICs)[1-3] that have recently become a focus of investigation in alcohol studies. This is due, in part, to the building evidence suggesting that P2XRs may be important mediators of ethanol-induced behavioral effects[4-7].

P2XRs are broadly distributed in the central and peripheral nervous systems[2,3,8]. Currently, seven subunits of the P2X family of LGICs have been identified (P2X1-P2X7). P2XR subunits form functional ATP-activated homomeric channels (e.g., P2X2, P2X4) as well as heteromeric receptors (e.g., P2X2/3, P2X4/6) in mammals[3,9]. P2XR channels are multimeric proteins where a functional receptor results from the assembly of three subunits[9-11]. P2X subunits consist of two transmembrane (TM) domains, a large extracellular domain (ectodomain) and intracellular amino-(N) and carboxy (C)-terminals (for review see[3,12]). Recent crystallographic investigations confirmed the trimeric structure of P2XRs with TM2 domains lining the pore[13]. The TM1 and TM2 membrane spanning segments are involved in ion channel gating and ion pore formation[14,15]. The ectodomain contains an ATP-binding site and is a site for channel regulation[2,3,16].

P2X2, P2X3 and P2X4Rs expressed in *Xenopus* oocytes are sensitive to ethanol at intoxicating concentrations[17-19]. Studies using a chimeric strategy that exploited the opposite effects of ethanol on P2X2R (ethanol inhibition) and P2X3R (ethanol potentiation) found that residues contained within the ectodomain-TM domain interfaces are important for mediating or modulating the threshold and magnitude of response of ethanol in P2X3Rs[5]. Extending the investigation to P2X4Rs resulted in the identification of two key residues at the ectodomain-TM2 interface (Asp331 and Met336) that, when substituted to alanine caused a significant reduction in ethanol (10-200 mM) inhibition of ATP-gated currents without causing marked changes in ATP $I_{max}$, $EC_{50}$ or Hill slope[6]. Additional studies exploring the relationship between structure and ethanol action found a significant correlation between hydropathy, polarity and the % inhibition by 50 mM ethanol of the residues at position 336[6]. Preliminary investigations using an alanine mutagenesis strategy identified position 46 (Trp46) contained within the ectodomain-TM1 interface as a potential target for the action of ethanol. Taken together, the findings support the hypothesis that the ectodomain-TM interfaces contain residues that are important for the action of ethanol in P2X4Rs.

Ivermectin (IVM) is a well tolerated, broad spectrum antiparasitic medication used in veterinary and human medicine[20,21]. Building evidence indicates that IVM can be used as a pharmacological tool for identifying the contribution of P2X4Rs in ATP-mediated processes[22]. Recent reports suggest that IVM binds at the lipid-protein interface acting on sites located in the TM segments at the ectodomain-TM domain interface of the P2X4R[23,24]. Individual mutations of residues at these interfaces indicated that positions Trp50, Val60 and Val357 may play an important role in IVM regulation of the rate of channel function[23,24].

Alcohol abuse and alcoholism affect an estimated 17 million people, cause over 100,000 deaths, and cost nearly $200 billion annually in the United States[36,37]. To address these issues, considerable attention has begun to focus on the development of medications to prevent and treat ethanol abuse and dependence[38-40].

SUMMARY OF THE INVENTION

Against this prior art background, the present invention provides a method for reducing alcohol consumption in a subject. The method comprises identifying a subject exhibiting at least one symptom of alcoholism and then administering a therapeutically effective amount of an Ivermectin analogue-containing composition to the subject. The Ivermectin analogue-containing composition comprising at least one Ivermectin analogue having the following formula:

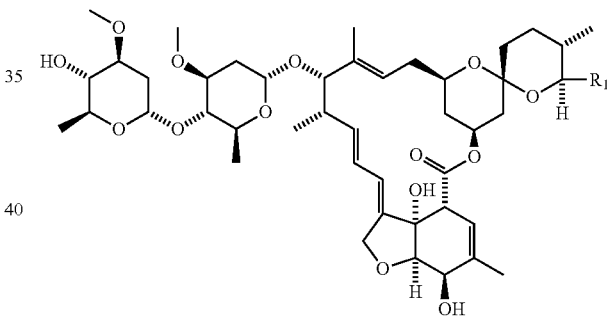

wherein $R_1$ is a $C_1$-$C_{10}$ alkyl.

In another embodiment, a method for reducing alcohol consumption in a subject is provided. The method comprises identifying a subject exhibiting at least one symptom of alcoholism and then administering a therapeutically effective amount of Ivermectin to the subject.

In still another embodiment, a method of identifying a candidate compound for reducing alcohol consumption in a subject is provided. The method includes a step of providing a membrane expressing P2X4R receptors. The membrane is contacted with a candidate compound which is an Ivermectin analogue. The response of the P2X4R receptors to the candidate compound is monitored. The candidate compounds are identified as potential compounds for reducing alcohol consumption in a subject if the candidate compound potentiates P2X4R receptor activity.

BRIEF DESCRIPTION OF THE DRAWINGS

Exemplary embodiments of the present invention will become more fully understood from the detailed description and the accompanying drawings, wherein.

DETAILED DESCRIPTION OF EXEMPLARY EMBODIMENTS

Figure 1:
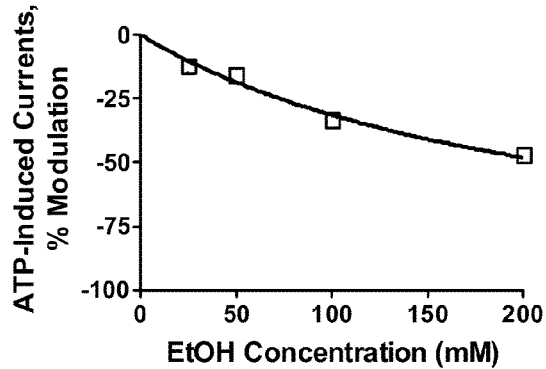
FIG. 1. Effects of ethanol and IVM in P2X4Rs. (A) Ethanol inhibits P2X4Rs in a concentration dependent and reversible manner. (B,C) IVM potentiates P2X4Rs in a concentration dependent and reversible manner. (B) Representative tracings of currents induced by ATP $EC_{10}$ and modulation of these currents by different concentrations of IVM. (C) Concentration response curve for IVM potentiation of P2X4Rs. Here and in other figures the effects of the drugs in wilde-type ("WT") P2X4Rs were tested using ATP $EC_{10}$ (1-1.2 µM). Data are presented as mean±SEM of 3-8 oocytes per data point. (D) Western blots showing that there is no change in the surface expression (biotinylated fraction) of P2X4Rs after treatment with IVM. Control—1 µM ATP; IVM, 20 s-3 µM IVM+1 µM ATP; IVM, 2 min—oocytes treated with 3 µM IVM for 2 min prior to addition of 1 µM ATP.
Figure 1:
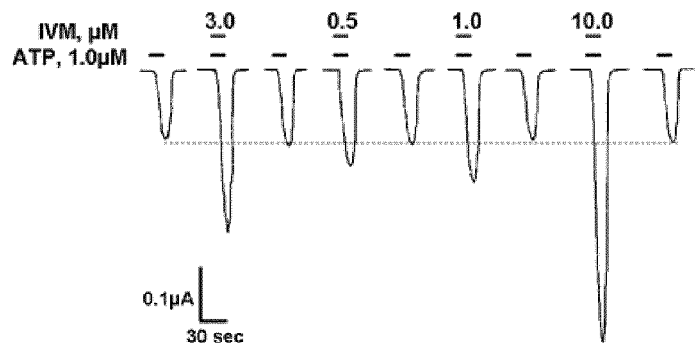
Figure 1:
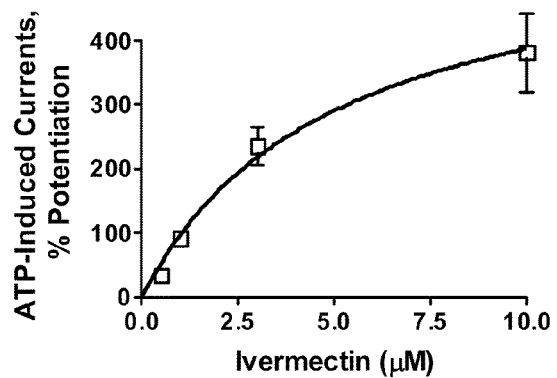
Figure 1:
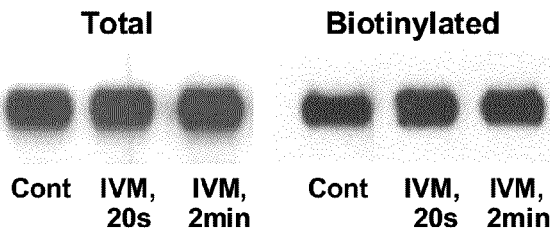

Reference will now be made in detail to presently preferred compositions, embodiments and methods of the present invention, which constitute the best modes of practicing the invention presently known to the inventors. The Figures are not necessarily to scale. However, it is to be understood that the disclosed embodiments are merely exemplary of the invention that may be embodied in various and alternative forms. Therefore, specific details disclosed herein are not to be interpreted as limiting, but merely as a representative basis for any aspect of the invention and/or as a representative basis for teaching one skilled in the art to variously employ the present invention.

Except in the examples, or where otherwise expressly indicated, all numerical quantities in this description indicating amounts of material or conditions of reaction and/or use are to be understood as modified by the word "about" in describing the broadest scope of the invention. Practice within the numerical limits stated is generally preferred. Also, unless expressly stated to the contrary: percent, "parts of," and ratio values are by weight; the description of a group or class of materials as suitable or preferred for a given purpose in connection with the invention implies that mixtures of any two or more of the members of the group or class are equally suitable or preferred; description of constituents in chemical terms refers to the constituents at the time of addition to any combination specified in the description, and does not necessarily preclude chemical interactions among the constituents of a mixture once mixed; the first definition of an acronym or other abbreviation applies to all subsequent uses herein of the same abbreviation and applies mutatis mutandis to normal grammatical variations of the initially defined abbreviation; and, unless expressly stated to the contrary, measurement of a property is determined by the same technique as previously or later referenced for the same property.

It is also to be understood that this invention is not limited to the specific embodiments and methods described below, as specific components and/or conditions may, of course, vary. Furthermore, the terminology used herein is used only for the purpose of describing particular embodiments of the present invention and is not intended to be limiting in any way.

It must also be noted that, as used in the specification and the appended claims, the singular form "a," "an," and "the" comprise plural referents unless the context clearly indicates otherwise. For example, reference to a component in the singular is intended to comprise a plurality of components.

The term "subject" refers to a human or animal, including all mammals such as primates (particularly higher primates), sheep, dog, rodents (e.g., mouse or rat), guinea pig, goat, pig, cat, rabbit, and cow. A subject is sometimes referred to herein as a "patient."

The term "therapeutically effective amount" means a dosage sufficient to cause reduced alcohol consumption in a subject. Such dosages may be administered by any convenient route, including, but not limited to, oral, parenteral, transdermal, sublingual, or intrarectal.

The term "Ivermectin analogue" refers to compounds having the ring structure of Ivermectin. In this context, the requisite ring structure does not consider unsaturation or subsituents on the rings. Ivermectin is a mixture of 5-O demethyl-22,23-dihydroavermectin $A_{1a}$ (at least 90%) and 5-O-demethyl-25-de(1-methylpropyl)-22,23-dihydro-25-(1-methylethyl)avermectin $A_{1a}$ (less than 10%). Ivermectin is also referred to as 22,23-dihydroavermectin $B_{1a}$ and $B_{1b}$, or $H_2B_{1a}$ and $H_2B_{1b}$, respectively. The present definition of Ivermectin analogue also includes Ivermectin.

In an embodiment of the present invention, a method for reducing alcohol consumption in a subject is provided. The method comprises identifying a subject exhibiting at least one symptom of alcoholism and then administering a therapeutically effective amount of an Ivermectin analogue-containing composition to the subject. The Ivermectin analogue-containing composition comprises at least one Ivermectin analogue having the following formula:

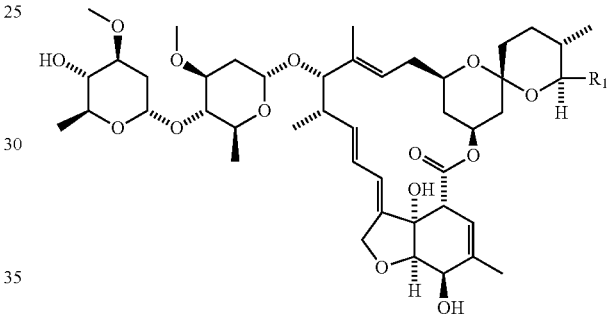

wherein $R_1$ is a $C_1$-$C_{10}$ alkyl. In a refinement, $R_1$ is non-cyclic $C_1$-$C_{10}$ alkyl. In another refinement, $R_1$ is methyl, ethyl, isopropyl, n-propyl, isobutyl, sec-butyl, or n-butyl. In still another refinement, $R_1$ is isopropyl, n-propyl, isobutyl, or sec-butyl. In a variation, the Ivermectin analogue-containing composition comprises Ivermectin.

In a variation of the present embodiment, the method further comprises monitoring alcohol consumption by the subject.

Ivermectin, which is formally an Ivermectin analogue, is described by the following formula:

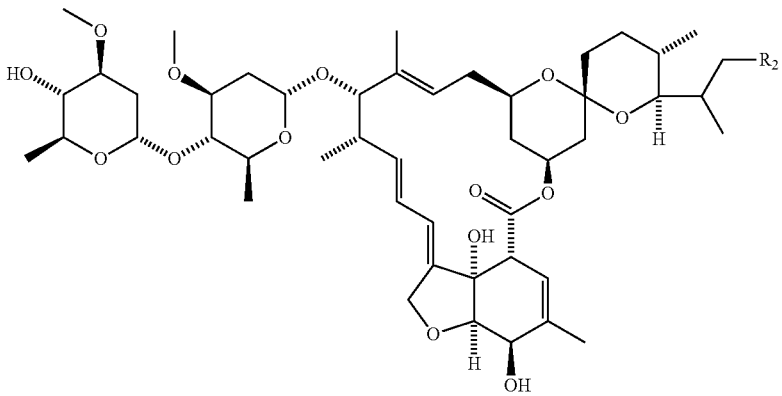

where for $B_{1a}$, $R_2$ is methyl and for $B_{1b}$, $R_2$ is hydrogen. Ivermectin typically contains more than 90% $B_{1a}$ and less than 10% $B_{1b}$.

Another Ivermectin analogue is Abamectin (ABM) which is described by the following formula:

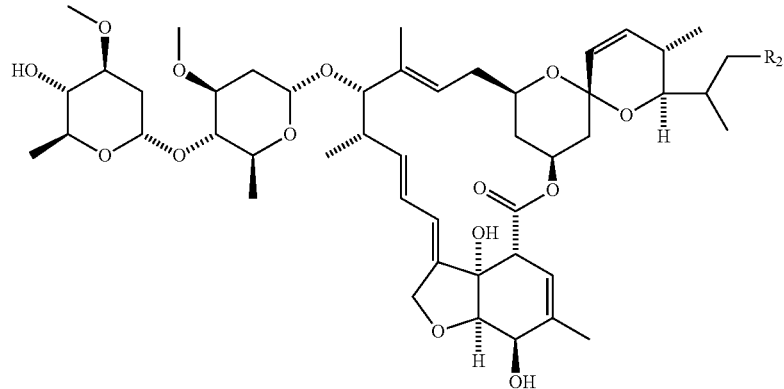

where for $B_{1a}$, $R_2$ is methyl and for $B_{1b}$, $R_2$ is hydrogen. Abamectin typically contains more than 80% $B_{1a}$ and less than 20% $B_{1b}$.

Another Ivermectin analogue is Selamectin (SEL) which is described by the following formula:

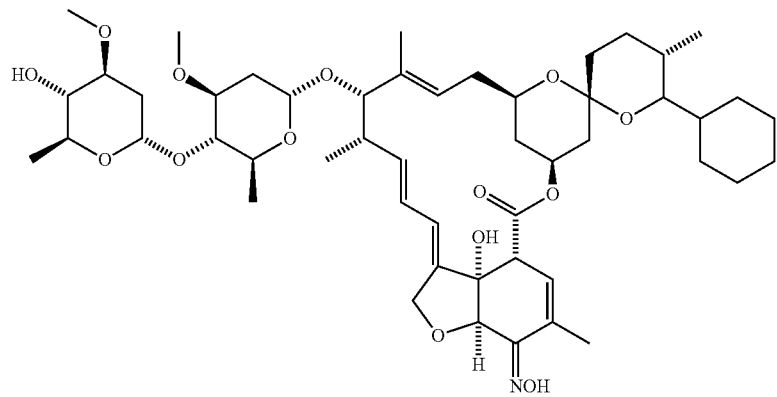

In another embodiment, a method of reducing alcohol consumption and/or symptoms of alcoholism in a subject is provided. The method comprises identifying a subject exhibiting one or more symptoms of alcoholism. A composition comprising a therapeutically effective amount of Ivermectin is administered to the subject exhibiting such symptoms. Symptoms that may be alleviated include, but are not limited to, the volume of alcohol the subject intakes.

In one variation, the amount of Ivermectin administered per day is from 0.025 to 0.1 mg per kg of weight (mg/kg) of a human subject. The human dose is determined by the ratios between humans and rodents for treatment of similar infestations. Therefore, the applicable dose for Ivermectin in humans should be between ⅛ and ½ of the typical dose used for parasites. In a refinement, the Ivermectin or Ivermectin analogue is administered in an amount of about 2 to about 8 mg/day for an average human subject weighing 80 kilograms. In another refinement, the Ivermectin or Ivermectin analogue is administered in an amount of about 3 to about 4 mg/day for an average human subject weighing 80 kilograms. In one variation, the Ivermectin or Ivermectin analogue is administered daily. In another variation, the Ivermectin or Ivermectin analogue is administered every other day. The Ivermectin or Ivermectin analogue may be administered over an extended period of time (a week to several months) depending on the subject's response. Typically, a human subject is treated for a period of 1 to 7 days so long as the Ivermectin is tolerated. In one refinement, the Ivermectin or Ivermectin analogue is administered for a period of one week. In another refinement, the Ivermectin or Ivermectin analogue is administered for a period of 2 to 3 weeks. Ivermectin is administered to the patient by any compatible method. Examples of such methods include, but are not limited to, oral and parenteral administration.

In another embodiment of the present invention, a method of identifying a candidate compound for reducing alcohol consumption and/or a symptom of alcoholism in a subject is provided. The method of this embodiment comprises providing a membrane expressing P2X4R. The membrane is contacted with a candidate compound. The response of the P2X4R receptors to the candidate compound is monitored. Candidate compounds potentiating P2X4R receptor activity are identified as potential compounds for reducing alcohol consumption in a subject and/or alleviating a symptom of alcoholism. Examples of Ivermectin analogues include, but are not limited to, compounds having the following formula:

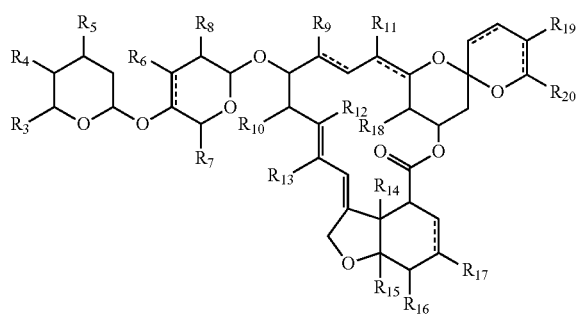

wherein:
$R_3$-$R_{20}$ are each independently $C_1$-$C_{10}$ alkyl, hydroxyl, =O, =NH, =$NR_{23}$, —$OR_{23}$, —SH, or —$SR_{23}$;
$R_{23}$ is $C_1$-$C_{10}$ alkyl; and
dashed line is absent or a bond.

In a refinement, the candidate compound has the following formula:

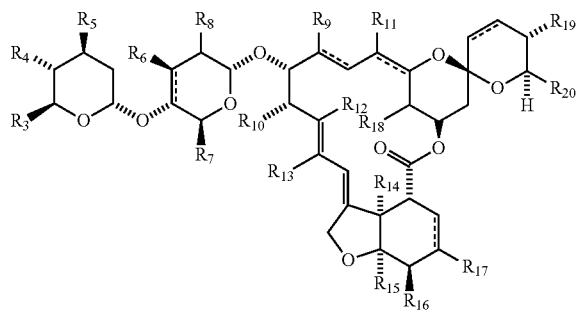

In a variation of the present embodiment, the method further comprises administering the candidate compound to a subject; and monitoring the level of alcohol consumed by the subject.

In a variation of this embodiment, a method of identifying a candidate compound for reducing alcohol consumption in a subject and/or alleviating a symptom of alcoholism is provided. The method of this embodiment comprises providing a first specimen of membranes expressing P2X4R receptors. The first specimen of membranes is contacted with a compound that is known to potentiate P2X4R receptor response. Examples of such compounds include, but are not limited to, Ivermectin and hexanol. The response of the P2X4R receptors to the compound that is known to potentiate P2X4R receptor response is quantified. A second specimen of membranes expressing P2X4R receptors is contacted with a candidate compound. The response of the P2X4R receptors to the candidate compound is quantified. If the candidate compound potentiates P2X4R receptor response, a third specimen of membranes expressing P2X4R receptors is contacted with a combination of the candidate compound and the compound that is known to potentiate P2X4R receptor response. The P2X4R receptor response to this combination is quantified. If the response to the combination is less than the sum of the individual responses to the candidate compound and the compound that is known to potentiate P2X4R receptor response, the candidate compound is identified as a potential compound for reducing alcohol consumption in a subject and/or alleviating a symptom of alcoholism. It should also be appreciated that in such situations, the candidate compound is a P2X4R antagonist.

In one refinement of the present embodiment, receptor responses are monitored and/or quantified by changes in ion flux. Ion flux is determined by measuring changes in ionic polarization (i.e., electrical potential) of a cell or membrane expressing P2X4R receptors. In a further refinement, ionic polarization changes are determined by measuring changes in current with voltage-clamp and patch-clamp techniques.

Although the operation of the embodiments of the invention is not dependent on any particular theory or mechanism of action, position 336 in P2X4Rs is identified as a possible site of ethanol action and antagonism by IVM. Taken in the context with recent genomic evidence that P2X4Rs may play a role in modulating alcohol consumption in rats[7], the present findings suggest that IVM is useful as a novel ethanol antagonist for reducing alcohol intake and alcohol-related problems. IVM is already used in humans as an anti-parasitic medication and thus could be developed rapidly as a novel therapeutic agent. These studies also suggest that the pocket comprised of position 336 and other key residues is a potential target for medication development for alcohol abuse.

It is also hypothesized that IVM interferes with or enhances the action of ethanol in these regions and thus alters the sensitivity of the receptor to ethanol since IVM appears to act on sites close to the sites found to be ethanol sensitive in the ectodomain-TM domain interface of P2X4Rs. The experimental data set forth below investigates the effects of IVM and ethanol on WT and mutant P2X4Rs with amino acids substitutions at position 336 expressed in *Xenopus* oocytes using two electrode voltage-clamps. The findings provide the first evidence that IVM antagonizes the effects of ethanol on P2X4Rs. In addition, the findings indicate that IVM antagonism of ethanol cannot be explained by additive interactions between IVM and ethanol at different sites, but are consistent with a mechanism of antagonism that involves interaction between IVM and ethanol at position 336 in P2X4Rs. Using the 3.1 A° resolution X-ray crystal structure of the zebrafish P2X4-A (PDB ID 3I5D)[13], a molecular model of the rat P2X4R is constructed demonstrating a pocket formed by Met336, Trp46 and Trp50 that may play a role in the action of ethanol and IVM.

The present study tested the hypothesis that IVM can affect ethanol sensitivity of P2X4Rs due to its action on sites closely located to those for ethanol. The experimental data set forth below support this hypothesis by demonstrating that IVM antagonizes the effects of ethanol in P2X4Rs. In addition, evidence that IVM and ethanol both act on position 336 at the ectodomain-TM2 interface is provided. The role of position 336 and other key residues in ethanol action are described in the context of a new molecular model of the rat P2X4R.

IVM alone, as previously reported[22,30], produced a concentration-dependent increase in ATP-activated currents in P2X4Rs. Prior studies suggested that this potentiation by IVM resulted from increased amplitude of ATP-induced currents and slowed deactivation[30]. Subsequent studies[25] suggesting that the mechanism might involve IVM-induced increase in the surface expression of the receptor were not supported by later studies that used surface biotinylation to determine receptor expression at 3, 5 and 10 minutes of IVM exposure[24]. The experimental section set forth below extends this result to demonstrate that in the presence of ATP, IVM does not change the amount of P2X4 surface expression at 20 seconds and two minutes after exposure. Therefore, the potentiating effect of IVM on P2X4R function in the present studies cannot be explained by changes in surface expression of the receptor.

The present findings are the first to show that IVM antagonizes the effects of ethanol. The degree of antagonism by IVM was inversely related to the ethanol concentration. The addition of 0.5 µM IVM completely eliminated the inhibitory effect of 25, 50 and 100 mM ethanol on ATP-activated currents without evidence of causing potentiation in P2X4Rs. An ethanol concentration of 25 mM is approximately 1.5 times the blood ethanol concentration (0.08%) that is considered the legal intoxication dose in the United States. Therefore, these findings support the notion that IVM is useful for antagonizing the effects of ethanol in humans.

The mechanism(s) by which IVM antagonized ethanol in P2X4Rs is not known. Nonetheless, several lines of evidence suggest that IVM antagonizes the inhibitory effect of ethanol by interfering with the action of ethanol on position 336 at the ectodomain-TM2 interface. First, IVM antagonism of ethanol could not be explained by the additive interaction of IVM potentiation on ethanol inhibition of P2X4R function. This suggests that the mechanism of antagonism involves competition at the same site and does not result from independent actions of these agents at different sites. This contention is supported by the non-additive interactions between IVM and the potentiating effects of hexanol on this receptor.

Second, mutations at position 336 altered the sensitivity of the receptor to modulation by both IVM and ethanol. In particular, substituting a positively charged bulky Arg or a negatively charged Glu at position 336 for the WT non-polar, bulky Met made the receptor insensitive to IVM and ethanol. These findings suggest that a charge at position 336, regardless of its nature, interferes with the initiation or transduction of the actions of IVM and ethanol. This effect suggests that a hydrophilic side chain or moiety could be critical for entrance/docking to a site at or near position 336. In this scenario, highly polar, charged substitutions at position 336 (i.e. Arg or Glu) might offer the greatest degree of repulsion, thus accounting for the abolishment of the ethanol effect. It is also possible that charged residues interact with other neighboring residues, thus causing structural changes in the above indicated region that decrease the interaction of IVM as well as ethanol with the receptor.

Moreover, substituting small non-polar amino acids (i.e., Ala, Val) for the bulky non-polar methionine markedly increased the receptor's sensitivity to IVM, but reduced it's sensitivity to ethanol[6]. If ethanol and/or IVM act on the receptor via complete or partial entry into a putative pocket that M336 is a part of, then these small residues may induce changes in the size of this hypothetical pocket. This, in turn, may increase the accessibility and subsequent docking of the larger IVM molecule and thus explain the increased potentiation. On the other hand, the change in the size of the pocket could reduce the interaction with ethanol leading to a decrease of ATP-gated currents. These findings add evidence for the importance of position 336 in the actions of both agents and demonstrate that varying the size of the residue at this position produces opposite effects on the magnitude of the receptors response to these agents. Collectively, these findings support the notion that position 336 plays an important role in initiating and/or transducing the actions of IVM and ethanol on P2X4Rs.

To examine possible interactions between the methionine at position 336 and other key residues thought to play a role in ethanol and/or IVM action[6,23], a homology model of the rat P2X4R using the recently published 3.1 Å X-ray crystal structure of zebrafish P2X4R[13] is constructed This model demonstrates that the Trp46 and Trp50 side chains of the first helix face Met336 in the final helix of the adjacent subunit. There is substantial literature about interactions of the antibonding orbitals of sulfur atoms with aromatic rings[31-33]. In addition, interactions of the sulfur atom of methionine residues with multiple aromatic groups have been referred to as "hot spots" in protein-protein interactions[34]. In the latter study, there are examples of multiple tryptophan or tyrosine rings oriented at right angles to each other, that is "edge on". In these conformations, the positive partial atomic charges of the aromatic ring hydrogens can interact with the face of a neighboring tryptophan ring in a cation-pi interaction[35]. Manual rotations of the C-alpha to C-beta bonds of Trp 46 and Trp 50 were sufficient to form a site in which the two Trp side chains and the sulfur of Met336 interact.

The possibility that an alcohol molecule could "bind" in this site by a combination of cation-pi interactions[36] between the hydrogen of ethanol and the tryptophans as well as additional interactions between the methionine sulfur atom and the oxygen atom of ethanol[33] is considered. To illustrate this point, an ethanol molecule is manually positioned in this site and showed that it fits nicely. It is noteworthy that the location of the three residues Trp46, Trp50 and Met336 forming the pocket is at the interface of the ectodomain and TM domains. In addition, the residues are in the region in P2X4R that Gouaux and co-workers suggested mediated transduction of binding energy between the ATP binding site and the constriction in the ion pore[13]. Testing of these suggestions must await future more elaborate docking of the ethanol molecule and long time-scale molecular dynamics studies. Nonetheless, this model of P2X4Rs revealed that several amino acid residues known to be important for the effects of alcohol on these receptors, although seemingly widely scattered in the primary sequence of P2X4R, were actually clustered around a small cavity in the 3-dimensional structure.

The following examples illustrate the various embodiments of the present invention. Those skilled in the art will recognize many variations that are within the spirit of the present invention and scope of the claims.

Ethanol and IVM Modulate P2X4Rs

In agreement with previous work[6,18], ethanol (25-200 mM) co-application with ATP inhibited ATP $EC_{10}$-induced currents in P2X4Rs in a concentration-dependent and reversible manner (FIG. 1A). Using the same protocol, IVM significantly potentiated $EC_{10}$ ATP-gated currents in P2X4Rs in a concentration-dependent and reversible manner (FIG. 1B,C).

Although controversial, recent findings suggest that IVM-induced increases of ATP-activated currents in P2X4R may reflect IVM-induced increase in cell surface expression[25], rather than a modulatory action on the receptor per se[24]. To assess this possibility, the affect of IVM on the surface expression of P2X4Rs in the oocyte preparations set forth herein is investigated using cell surface biotinylation in combination with Western blotting. The results indicate that oocyte incubation with IVM in the presence of ATP did not change the surface expression levels of P2X4Rs in oocytes (FIG. 1D). This lack of change in cell surface expression is consistent with the notion that IVM potentiates ATP-gated current in P2X4Rs by direct action on the receptor.

IVM Antagonizes Ethanol Inhibition of P2X4Rs

Figure 2:
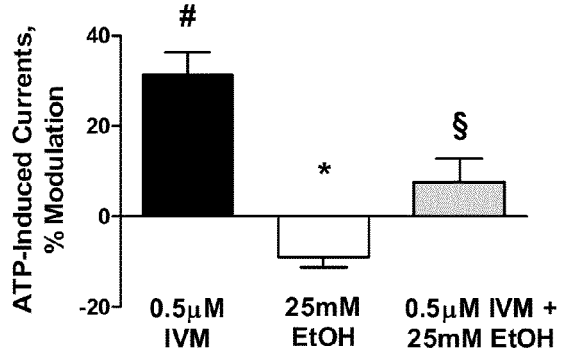
FIG. 2. Individual and combined effects of IVM and ethanol in P2X4Rs. (A) IVM (0.5 µM) completely antagonizes the inhibitory effect of 25 mM ethanol on ATP-induced currents. *, #-$P<0.05$ compared to ATP only, §-$P<0.05$ compared to ATP+ethanol. (B) The degree of IVM antagonism of ethanol inhibition is dependent on the concentration of IVM and ethanol. IVM 0.5 µM antagonizes the response to 50 and 100 but not to 200 mM ethanol. IVM at 1 and 3 µM antagonize the inhibition induced by all concentrations of ethanol (50, 100, 200 mM). *$P<0.05$ compared to ethanol data. (C) Representative tracings showing modulation of ATP-induced currents by individual applications of IVM (1 µM) and ethanol (50, 100, 200 mM) and the antagonistic effect of IVM on ethanol inhibition during their combined action. Horizontal short bars above the currents depict ATP or drug applications. Numbers next to the short bars represent ethanol concentrations. Dotted line represents the baseline responses for ATP. Horizontal bar denotes 60 sec, vertical –0.2 µA. Data are presented as mean±SEM of 5-10 oocytes per data point.
Figure 2:
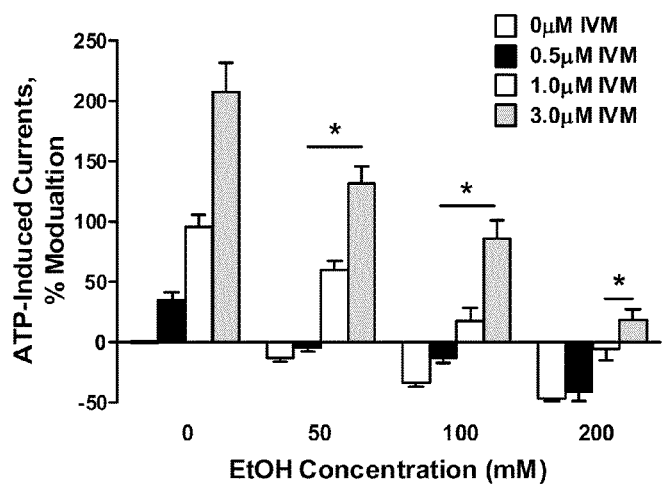
Figure 2:
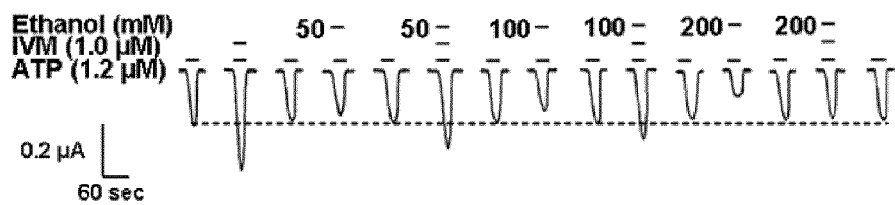

To determine the effect of IVM on ethanol inhibition of P2X4Rs, the effect of 0.5 µM IVM was tested alone or in combination with a behaviorally relevant concentration of ethanol (25 mM) on ATP-activated currents in P2X4Rs. As expected, when delivered separately, ethanol significantly inhibited (9±2.3%) and IVM significantly potentiated (31±4.9%) ATP-gated currents in P2X4Rs (FIG. 2A). When co-applied with ethanol, IVM completely antagonized the inhibitory effect of ethanol (FIG. 2A).

To further study the mechanism of the antagonism, concentration response studies were conducted. For that, applied several concentrations of IVM (0.5-3 μM) were individually applied with increasing concentrations of ethanol (50-200 mM). IVM antagonized ethanol inhibition (FIG. 2B). Moreover, the degree of antagonism was dependent on the concentration of IVM tested with higher concentrations of IVM (1.0 and 3.0 μM) completely antagonizing the inhibitory effects of ethanol at all ethanol concentrations (50-200 mM; FIG. 2B,C). The lower concentration of IVM (0.5 μM) also completely antagonized the inhibitory effects of 50 and 100 mM ethanol. On the other hand, 0.5 μM IVM did not significantly alter the effect of the highest concentration of ethanol (200 mM).

Figure 3:
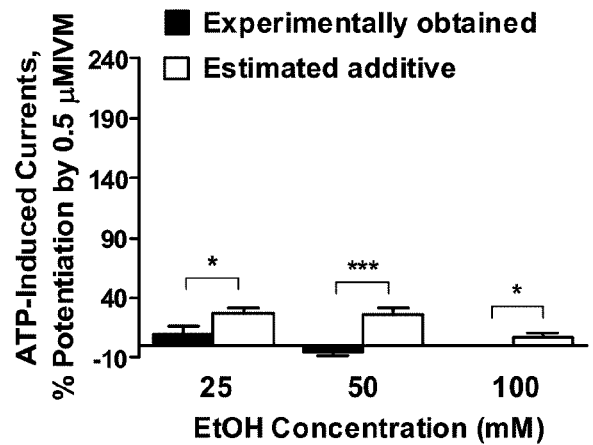
FIG. 3. Comparison of experimentally obtained data of the combined effects of IVM and ethanol (black bars) and estimated additive values of the effects of individual drugs (empty bars). Significant differences between these groups were found at (A) 0.5 µM, (B) 1 µM and (C) 3 µM concentrations of IVM and different concentrations of ethanol. *$P<0.05$, **$P<0.01$. Data are presented as mean±SEM of 5-10 oocytes per data point.
Figure 3:
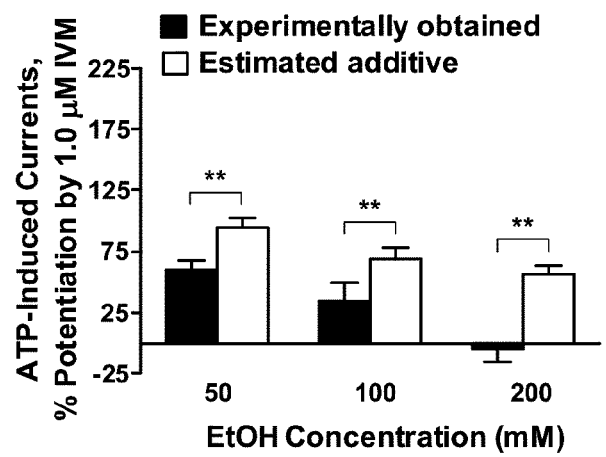
Figure 3:
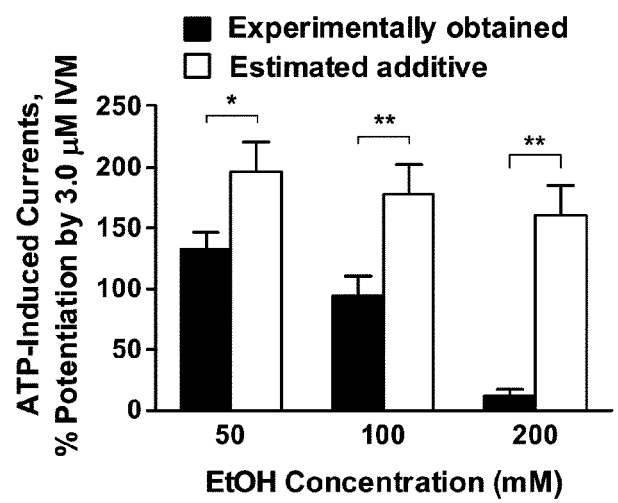

Since IVM and ethanol had opposite effects on ATP-gated currents, the antagonistic effect of IVM could result from an addition of these opposing effects. The latter possibility is supported by the net potentiation observed when high concentrations of IVM were co-applied with ethanol (FIG. 2B). To assess this possibility, the experimentally obtained results (presented in FIG. 2B) are compared to the estimated additive values of the individual effects of the two drugs. As shown in FIG. 3, the experimentally obtained data of combined action of IVM (0.5, 1 and 3 μM) and ethanol at 50, 100, 200 mM (FIG. 3A,B,C) were significantly lower than the estimated additive values of the effects of the two drugs obtained individually. These findings indicate that IVM antagonism of ethanol cannot be explained by additive interactions and are consistent with a mechanism of antagonism that involves interaction between ethanol and IVM at a common site in P2X4Rs.

This possibility was investigated by testing the effects of IVM on another n-chain alcohol. Previous investigations report that short chain alcohols potentiate, whereas long chain alcohols inhibit, native nicotinic acetylcholine receptors (nAChRs) contained in neuromuscular or Torpedo preparations[26]-28. This alcohol crossover occurred at approximately butanol in nAChRs expressed in Xenopus oocytes[29]. Additional investigations suggest that there is also crossover with alcohols when tested in P2XRs. That is, these additional studies found that ethanol and propanol inhibit P2X2R function, whereas butanol potentiates P2X2R function (unpublished data). It is believed that testing an alcohol that produced potentiation, rather than inhibition, would provide an alternative method of determining if the interaction between ethanol and IVM represented an additive effect.

Figure 4:
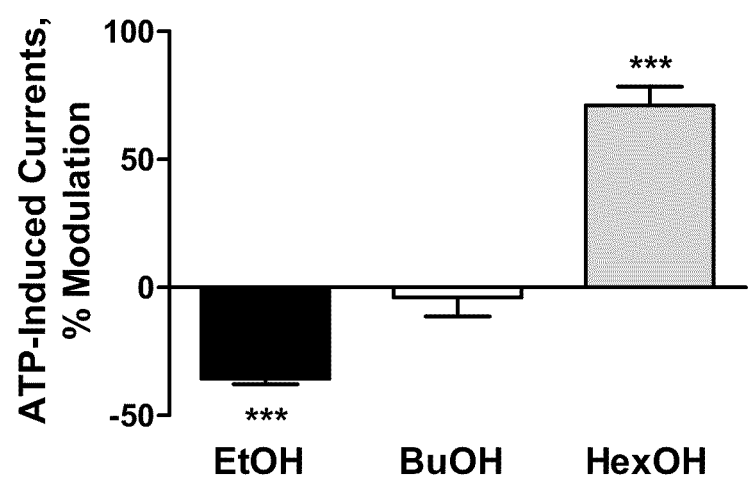
FIG. 4. Effects of different n-chain alcohols in P2X4Rs. Ethanol (C2, 200 mM) inhibited, butanol (C4, 50 mM) produced minimal effect, whereas hexanol (C6, 10 mM) significantly potentiated ATP-induced currents in P2X4R. The hexanol potentiation represents a crossover effect from inhibition induced by ethanol. ***$P<0.001$ compared to ATP only. Data are presented as mean±SEM of 12-16 oocytes per data point.

The effects of ethanol, butanol and hexanol were studied on ATP-induced currents to determine if either butanol or hexanol would cross over and potentiate ATP-gated currents in P2X4Rs. Butanol (C4) produced minimal effects on P2X4R function, whereas, hexanol (C6) produced significant potentiation (FIG. 4). This finding demonstrates a crossover from inhibition to potentiation as the n-chain length increases between butanol and hexanol in P2X4Rs.

Figure 5:
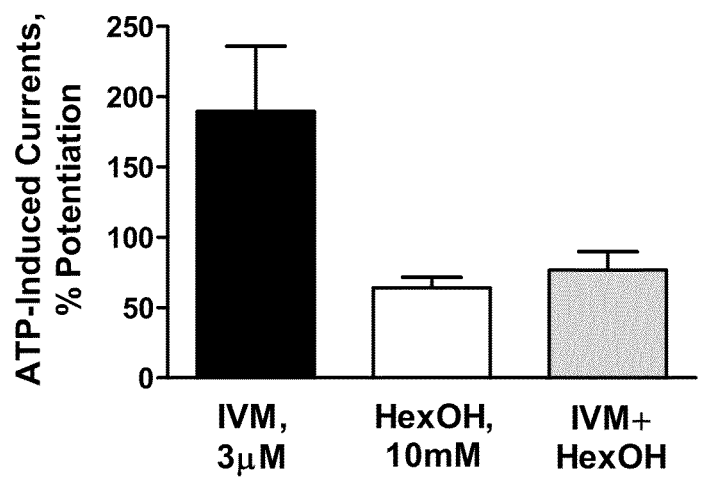
FIG. 5. Individual and combined effects of IVM and hexanol in P2X4Rs. (A) IVM (3 µM) and hexanol (10 mM) significantly potentiated ATP-induced currents when applied individually or in combination. $P<0.05$ compared to ATP only. (B) Representative tracings showing modulation of ATP-induced currents by individual applications of IVM (3 µM), hexanol (10 mM) and co-application of IVM and hexanol. Horizontal short bars above the currents depict ATP or drug applications. Numbers next to the short bars represent hexanol concentration. Dotted line represents the baseline responses for ATP. Horizontal bar denotes 30 sec, vertical—0.1 µA. (C) Comparison of experimentally obtained data of the combined effects of IVM and hexanol (black bar) and estimated additive value of the effects of individual drugs (empty bar) shows a significant difference. **$P<0.01$. (A,C) Data are presented as mean±SEM of 3-5 oocytes per data point.
Figure 5:
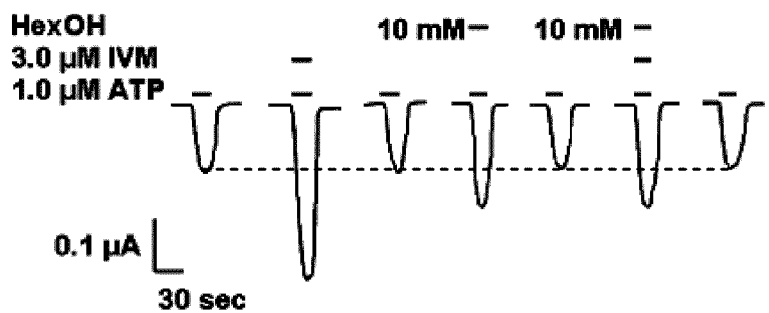
Figure 5:
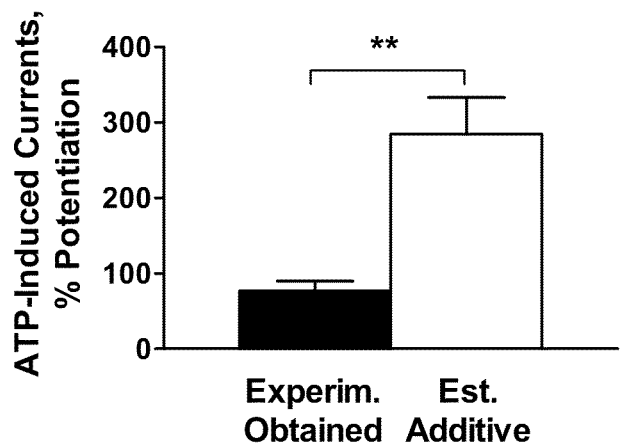

Given that both IVM and hexanol each potentiated P2X4R function when applied individually, the combination of the two is predicted to produce greater potentiation than each individually if their effects were additive. In contrast, if they competed for the same site, the interaction should reduce the overall potentiation. The results support the latter possibility (FIG. 5A,B). That is, the net result of exposure of P2X4Rs to both IVM and hexanol is significantly less than would be anticipated from additive effects (FIG. 5C). These data added further support for the notion that the antagonism of ethanol inhibition by IVM involves interaction between ethanol and IVM at a common site in P2X4Rs.

Position 336 is Important for the Action of IVM

Recent work found that amino acid substitutions at position 336 in the ectodomain-TM2 interface of P2X4Rs can significantly reduce or eliminate the effects of ethanol. These findings indicate that position 336 is important for ethanol modulation[6]. Coupled with previous work suggesting that IVM interacts with the TM domains at the ectodomain interface[24], prior findings with ethanol are consistent with a hypothesis that position 336 may also play a role in IVM action.

Figure 6:
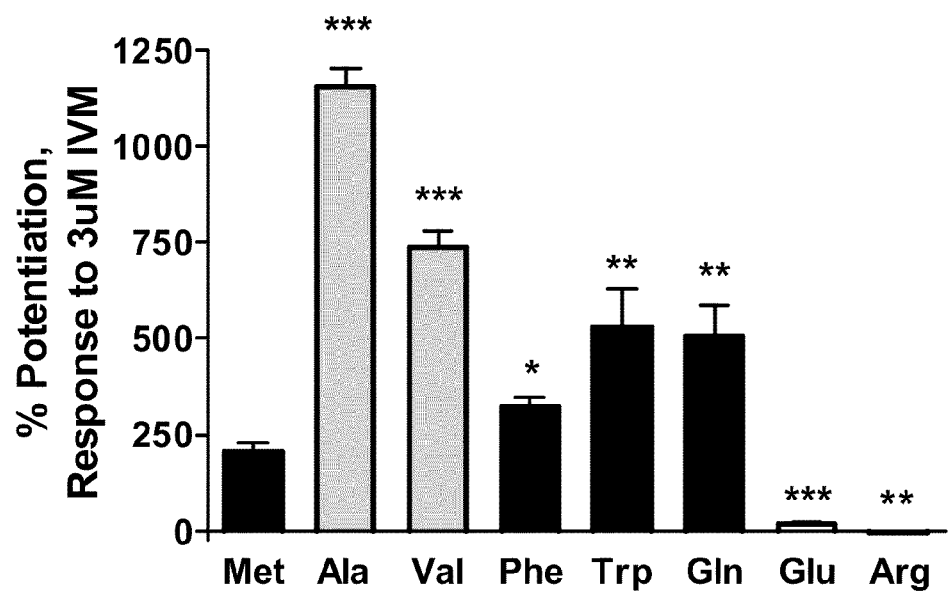
FIG. 6. Effects of IVM in mutant P2X4Rs receptors at position 336. Amino acid substitutions with different physical-chemical properties at position 336 significantly alter sensitivity to IVM (3 µM). Substitutions of WT bulky non-polar residue (Met) with small non-polar (Ala, Val) or bulky non-polar (Phe, Trp) or bulky polar (Gln) residues significantly increase the degree of IVM potentiation compared to WT P2X4Rs. Substitution with charged residues (Glu, Arg) eliminate the IVM potentiation. Data are presented as mean±SEM of 3-10 oocytes per data point. *$P<0.05$, $P<0.01$, *$P<0.001$ compared to WT P2X4Rs.

To explore this possibility, the effect of position 336 substitutions was tested with different physical-chemical properties on the response to IVM. One or more of these substitutions are predicted to significantly alter IVM sensitivity if position 336 plays a role in the action of IVM. Prior work had successfully used this approach with ethanol[6]. Therefore, key substitutions at position 336 that altered ethanol sensitivity[6] were tested. As shown, amino acid substitutions that previously altered the effects of ethanol also significantly altered IVM sensitivity (FIG. 6). These findings support the hypothesis that position 336 is important for both IVM and ethanol modulations of P2X4R function.

The results from these mutations at position 336 provide insight into the physical chemical properties at position 336 that affect sensitivity to IVM. Substituting Met336 with the small non-polar Ala or Val residues markedly increased the degree of IVM potentiation (FIG. 6). Substituting the bulky non-polar Phe or Trp residues increased IVM potentiation, but less so than with the non-polar amino acids. Substituting Met with the polar bulky Gln residue had approximately the same effect on IVM sensitivity as substituting the non-polar bulky residues (FIG. 6). Substituting charged positive (Arg) or negative (Glu) amino acids for the bulky non-polar Met eliminated sensitivity to IVM (FIG. 6). Taken together, the current IVM findings indicate there is an inverse relationship between the size of the amino acid at position 336 and the degree of IVM potentiation. It is noteworthy that charged bulky residues, whether positive or negative, abolished sensitivity to IVM. Therefore, it appears that the size and the charge of the substitutions at position 336 play key roles in determining sensitivity to IVM. It is remarkable that these same physical chemical properties of the residue at position 336 also played key roles in determining ethanol sensitivity without significantly altering basic receptor function[6]. Together, the findings with IVM and with ethanol add further evidence that position 336 is a target for both ethanol and IVM action in P2X4Rs.

Molecular Modeling of the Rat P2X4R Determines the Position of Met336

Figure 7:
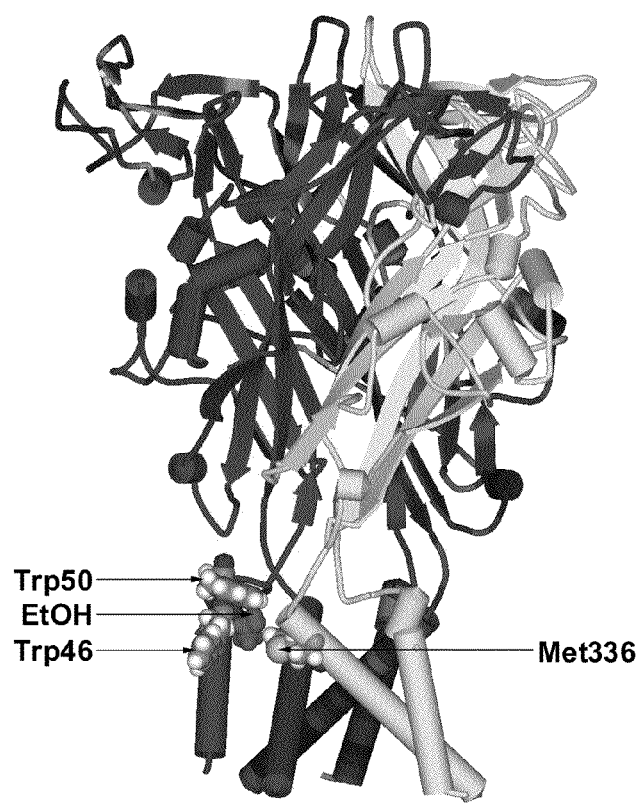
FIG. 7. Molecular model of the rat P2X4R built by threading the edited primary sequence onto the X-ray crystal structure of zebrafish P2X4R. Represents a side view of the rat P2X4R showing the ectodomain and the six alpha helices of TM1 and TM2 segments of 3 different P2X4R subunits. All residues of interest were rendered as space filling surfaces; the ethanol molecule is colored pink to distinguish it. Residues W46, W50 in the first alpha helix of one subunit and M336 in the final alpha helix of the adjacent subunit form a pocket that demonstrates a good fit for a molecule of ethanol at the same scale.

To visualize the potential molecular interactions of Met336 and other key residues and their potential role in IVM antagonism of ethanol action, a homology model of the rat P2X4R was generated. The model is based on the crystal structure of zebrafish P2X4R[13]. The resultant model is shown in FIG. 7. Based on the current and prior studies reviewed in the Introduction, the figure highlights residues Trp46 and Trp50 in the first alpha helix of one subunit and Met336 in the final alpha helix of the adjacent subunit. The location of the three residues Trp46, Trp50 and Met336 is at the interface of the ectodomain and TM domains. Manual rotations of the C-alpha to C-beta bonds of Trp46 and Trp50 were sufficient to form a site in which the two Trp side chains and the sulfur of Met336 interact (FIG. 7). The Trp46 and Trp50 side chains of the first helix faced toward Met336 in the final helix of the adjacent subunit creating a putative pocket in which an ethanol molecule was manually positioned.

Methods

Materials. Adenosine 5'-triphosphate disodium salt, ethanol (190 proof, USP), IVM, collagenase were purchased from Sigma Co. (St. Louis, Mo., USA). 10 mM stock solutions of IVM were made in DMSO and kept at −20° C. The highest DMSO concentration in final solutions was 0.1%. All other chemicals were of reagent grade.

Isolation of *Xenopus Laevis* oocytes and cRNA injections. *Xenopus* oocytes were isolated and maintained as described previously[18,19]. All procedures for the maintenance of *Xenopus Laevis* frogs and oocyte isolation were approved by The Institutional Animal Care and Use Committee of the University of Southern California. Stage V and VI oocytes were used for cRNA (0.01-5 ng) injections using Nanoject II Nanoliter injection system (Drummond Scientific, Broomall, Pa.) one day after isolation. Injected oocytes were stored at 16° C. in incubation medium containing (in mM), NaCl 96%, KCl 2%, $MgC_{l2}$ 1%, $CaC_{l2}$ 1%, HEPES 5%, theophylline 0.6, pyruvic acid 2.5, with 1% horse serum and 0.05 mg/ml gentamycin. The oocytes were used in electrophysiological recordings for 3-10 days after cRNA injections.

Site-directed mutagenesis and cRNA synthesis. The cDNA of rat P2X4R (GenBank accession No. X87763) was subcloned into pcDNA3 vector (Invitrogen, Carlsbad, Calif.). Mutagenesis was performed to introduce single point mutations using QuickChange IIXL Site-Directed Mutagenesis kit (Stratagene, La Jolla, Calif.). The sequences of mutant constructs were verified using automated DNA sequencing (USC/Norris DNA Core Facility, University of Southern California).

The DNA of WT or mutant receptors was linearized and transcribed using the mMESSAGE mMACHINE kit (Ambion, Austin, Tex.) to result in cRNA, which was stored at −70° C. until injection.

Whole-cell voltage-clamp recordings. Two-electrode voltage-clamp recordings of oocytes were performed using a Warner Instruments Model OC-725C oocyte clamp amplifier (Hamden, Conn.) using procedures published earlier[5,6].

Experimental procedures. To induce currents and test the effects of alcohols and IVM in the present experiments, maximal (100 μM) or submaximal ATP concentrations ($EC_{5-10}$ furthered referred to as $EC_{10}$) were used. It has been previously shown that the use of $EC_{10}$ can maximize the effects of ethanol and minimize receptor desensitization 18,19. The washout time between agonist applications was at least 5-10 min to allow complete re-sensitization of the receptors[18, 19].

Effects of the drugs were tested after a stable response to ATP $EC_{10}$ was obtained. After a sufficient washout time (5-15 min), the cells were challenged with the same ATP $EC_{10}$ to ensure an accurate response to the drugs and to asses any change in the baseline level.

IVM and alcohol applications. Alcohols (ethanol, butanol and hexanol) were co-applied with ATP $EC_{10}$ for 20 sec[19]. To allow comparison of the effects of IVM with those of ethanol, the same co-application protocol was used for IVM. Alcohols and IVM did not affect the resting membrane currents in uninjected oocytes nor did either drug induce any currents when applied without ATP. To study the simultaneous effects of IVM and alcohols (either ethanol or hexanol), both drugs are co-applied with ATP $EC_{10}$. UV spectra of IVM (OD244 nm) were measured in the presence of differing concentrations of ethanol. No change in the UV characteristics confirmed that IVM and ethanol did not interact in the solution.

Surface biotinylation and Western blotting. Oocytes expressing P2X4R cRNA were treated with 3 μM IVM in the presence and absence of 1 μM ATP and incubated with 1.0 mg/ml membrane-impermeable sulfo-NHS-SS-biotin (Pierce Biotechnology, Rockford, Ill.) for 1 hr on ice. After lysis, the biotinylated proteins were precipitated by overnight incubation with streptavidin beads (Pierce Biotechnology) and extracted using SDS sample buffer. Protein lysates of total and biotinylated fractions were then run on 10% SDS-PAGE, transferred to PVDF membranes and blotted with a rabbit P2X4R antibody (Millipore, Temecula, Calif.). Following incubation with the secondary anti-rabbit antibody, the P2X4R bands were visualized using enhanced chemiluminescence (Pierce Biotechnology).

Molecular modeling. The 3.1 A° resolution X-ray crystal structure of the zebrafish P2X4-A (PDB ID 3I5D)[13] was used as a template for the homology models of the rat P2X4R. The PDB file of 3I5D has unresolved electron density at the N-terminal and C-terminal ends. As a result, the primary sequence of rat P2X4R was edited to fit the length of the zebrafish P2X4R structure before sequence alignment. The homology was high and it was possible to align the sequences without gaps. The rat sequence was threaded onto the backbone atoms of the template using the Modeler module of Discovery Studio 2.1 (Accelrys, San Diego, Calif., USA), essentially as previously described for GABAAR and GlyR models[41]. The auto-rotomer module of Discovery Studio was used to optimize the positions of the side chains while the backbone atoms were tethered. The resulting model was relaxed by tethering the backbone atoms with a harmonic restraint of 10 $kcal/A^2$, then optimizing to a gradient of 0.001 kcal/A, and running molecular dynamics for 10,000 1 fs steps at 300K. A molecule of ethanol at the same scale was built and manually positioned near the obvious site between these residues. In order to accommodate the ethanol molecule better, the C-alpha to C-beta bond of both tryptophan side chains was rotated and then manually repositioned the ethanol in the resulting cavity.

Data analysis. Data are obtained from several batches of oocytes of at least 3 different frogs and are expressed as mean±SEM. Ethanol (hexanol) and/or IVM effects are presented as percentage change of peak currents evoked by ATP $EC_{10}$ alone. Data were fitted to a concentration-response curve by using the following logistic equation: $I=I_{max}*[drug]/([drug]+(EC_{50}))$, where $I/I_{max}$ is the percentage of the maximum obtainable response, $EC_{50}$ is the concentration producing a half-maximal response. GraphPAD Prism software (San Diego, Calif.) was used for data analysis and curve fitting. Statistical analysis was performed using unpaired t-test with significance set at $P<0.05$.

Modulation of Alcohol Consumption in Mice

The role of P2X4R receptor in modulating alcohol consumption was tested by investigating the ability of IVM to reduce ethanol intake in ethanol preferring C57BL/6 mice using a two-bottle choice paradigm. In a first set of experiments, mice were individually housed with access to 2 bottles containing tap water for 4 days to establish baseline water consumption. Then, one bottle was replaced with a bottle containing a 10% v/v ethanol solution (10E) for 4 days, with a position change of the ethanol bottle each day to avoid side preferences. Daily fluid intake was measured by weight. Two groups of mice (n=12), matched on their baseline water consumption, were injected intraperitoneally with either saline or IVM (10 mg/kg) immediately prior to each day of access to 10E versus water. Repeated measures ANOVA revealed a strong trend for IVM to decrease daily 10E preference with preference significantly lower on day 3. IVM also tended to reduce average preference although the reduction in ethanol dose consumed was not significant. While IVM produced a non-significant reduction in ethanol intake, the alteration in ethanol preference may have been due to a significant increase in average water consumption by IVM.

Figure 8:
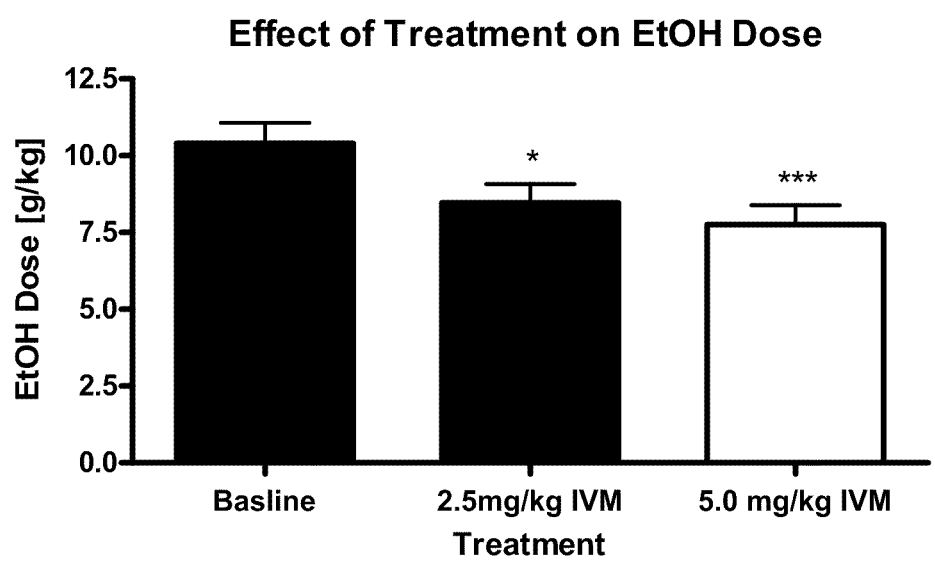
FIG. 8. IVM significantly reduces ethanol consumption in C57BL/6 mice in a dose dependent manner. Mice received a daily injection with saline or IVM (2.5 or 5.0 mg/kg) immediately prior to each day of 24 hr access to 10E versus water. Ethanol drinking was allowed to stabilize at approximately 10 g/kg prior to testing (Baseline drinking level for mice). Values are the mean±SEM for n=15 within subjects design. *$P<0.05$, ***$P\leq0.001$ versus Baseline value of ethanol consumption with saline injections.

Based on the initial experiments, a second study was conducted using a similar research design strategy with the following changes. Using a within subjects design, alcohol drinking was allowed to stabilize (based on DOSE approximately 10 g/kg) with a new set of C57Bl mice (n=15). Once alcohol intake stabilized at approximately 75% preference, the animals were injected with saline and re-tested to ensure that the injection, per se, did not have any affect on drinking behavior and to habituate the animals to the handling. After three days of saline injections (to ensure that the level of ethanol drinking remained constant), the mice were injected with a single injection of IVM (2.5 mg/kg). On intervening days, the mice were injected with saline. After 3 days of saline injections (allowing for alcohol drinking to restabilize back to 'baseline' levels), the mice were injected with a single, higher dose of IVM (5.0 mg/kg). Once again drinking was allowed to re-established back to baseline. Using repeated measures of ANOVA, we found that treatment with IVM significantly reduced ethanol consumption in the mice (FIG. 8). Taken together, these initial findings indicate that IVM reduces alcohol consumption in a dose dependent manner.

Overall, these initial results suggest that IVM reduces the acquisition of 24 hr ethanol preference in animals. Taken in context with our in vitro IVM/ethanol findings and recent genomic evidence that P2X4Rs may play a role in modulating alcohol consumption, the present findings suggest that IVM may have potential as a novel ethanol antagonist for reducing alcohol intake and alcohol-related problems.

Comparison of Ivermectin Analogues

Isolation of *Xenopus* Oocytes and cRNA Injections. *Xenopus laevis* frog (Nasco; WI) maintenance, oocyte isolation and cRNA injections were performed according to protocols as described previously (11,12,24).

Transcription of cDNA to cRNA. XL-Blue *E. coli* competent cells (Stratagene; CA) were transformed with rat WT P2X4 receptor cDNAs cloned into pcDNA3 vector (Invitrogen; CA). The isolated DNA was linearized and transcribed to result in capped cRNA, which was dissolved in nuclease-free water and stored at −70° C. until injection.

Whole-Cell Voltage Clamp Recording. Two-electrode voltage-clamp recording of oocytes was performed using a Warner Instruments Model OC-725C oocyte clamp. Electrodes were prepared and used to impale the oocyte that was continuously perfused at the rate of 3-4 ml/min by extracellular bathing solution per procedures previously published (11,12,24). The peak currents recorded using a strip-chart recorder (Barnstead/Thermolyne, Iowa) were used in data analysis. All experiments were performed at room temperature (20-23° C.).

Experimental Procedures. Maximal ATP currents were induced by 15 s application of 100 µM ATP. Submaximal ATP concentrations ($EC_{10}$) were applied for 20 s to generate currents. Ethanol and ABM/IVM were co-applied with ATP EC10. Washout time between drug applications was at least 5 min.

Data Analysis. Data are obtained from several batches of at least 3 different oocyte batches and are presented as percentage change of peak currents evoked by ATP EC10 alone±SEM. GraphPAD Prism software (San Diego, Calif.) was used for data analysis and curve fitting. Statistical analysis was performed using Student's unpaired t-test and significance set at $P<0.05$.

Figure 9A:
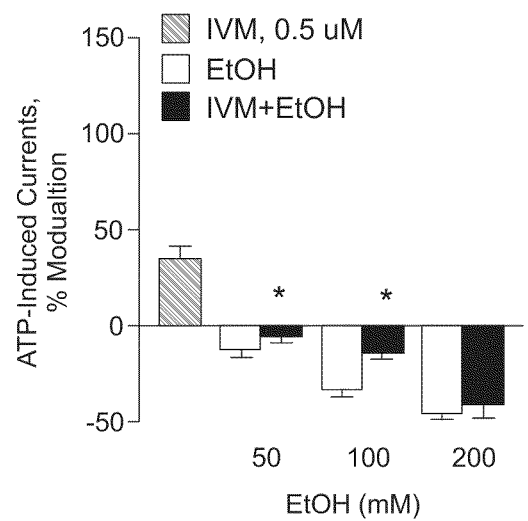
FIG. 9A provides a histogram of the percent modulation of ATP-Induced currents at various ethanol concentrations for IVM at 0.5 mM, ethanol, and IVM plus ethanol.
Figure 9B:
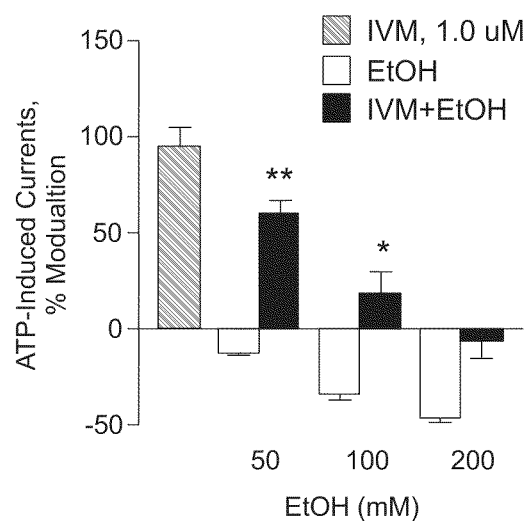
FIG. 9B provides a histogram of the percent modulation of ATP-Induced currents at various ethanol concentrations for IVM at 0.1 mM, ethanol, and IVM plus ethanol.
Figure 9C:
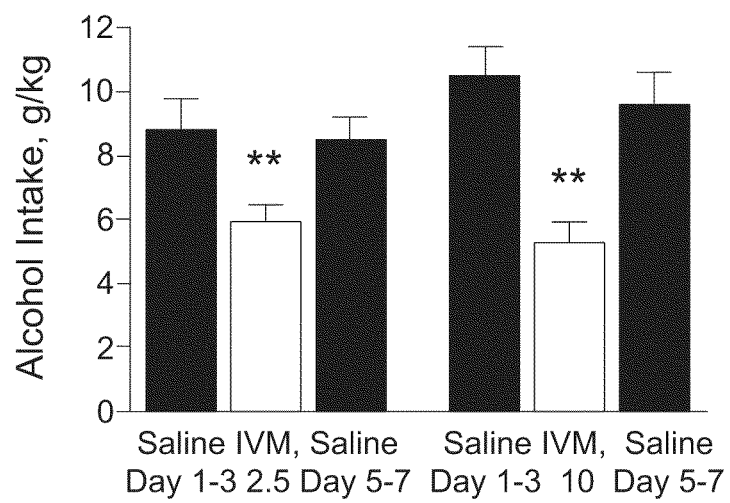
FIG. 9C provides a histogram showing that IVM induces decreased consumption of alcohol in mice.

FIGS. 9A and B provided histograms showing that Ivermectin (IVM) antagonizes the inhibitory effects of ethanol when co-applied with ethanol. *$P<0.05$, $P<0.01$ compared to the ATP+ethanol, n=7-20. FIG. 9A shows that IVM antagonizes ethanol effects in the oocyte expression system. Moreover, FIG. 9B shows that IVM decreases ethanol intake in mice. FIG. 9C provides a histogram showing that IVM decreases alcohol consumption (32 and 50% for 2.5 and 10 mg/kg doses respectively) in male C57BL/6 mice using a 24 hour access model after establishing a stable baseline drinking level (10% alcohol). $P<0.01$, n=16/group.

Figure 10A:
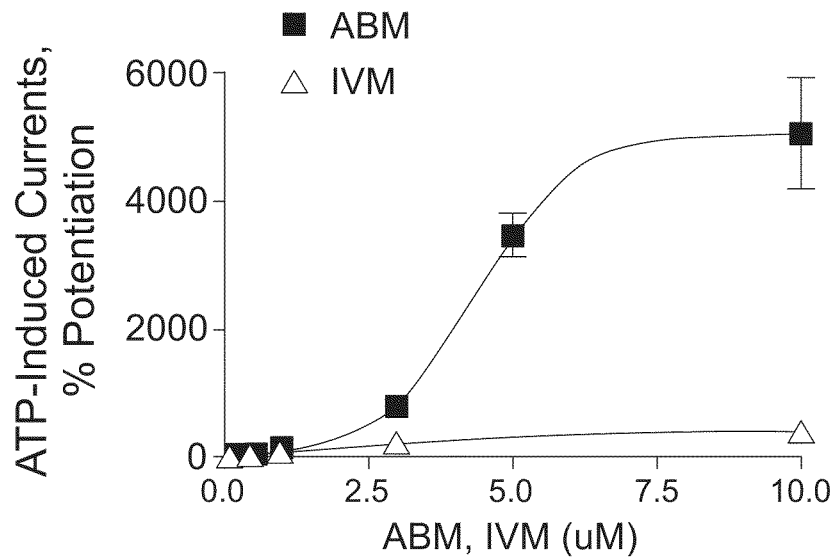
FIG. 10A provides plots of the percent potentiation for ATP-Induced currents versus AMB and IVM concentration.
Figure 10B:
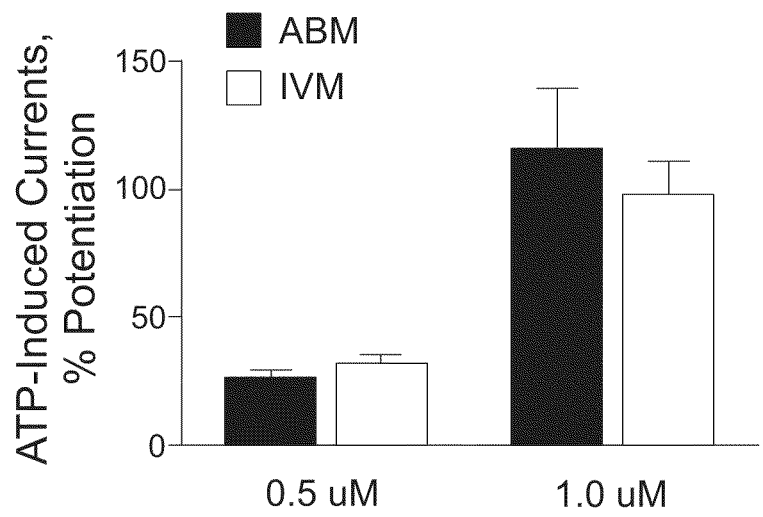
FIG. 10B provides a histogram of the percent potentiation for ATP-Induced currents for 0.5 µM and 1.0 µM concentrations of AMB and IVM concentration.
Figure 10C:
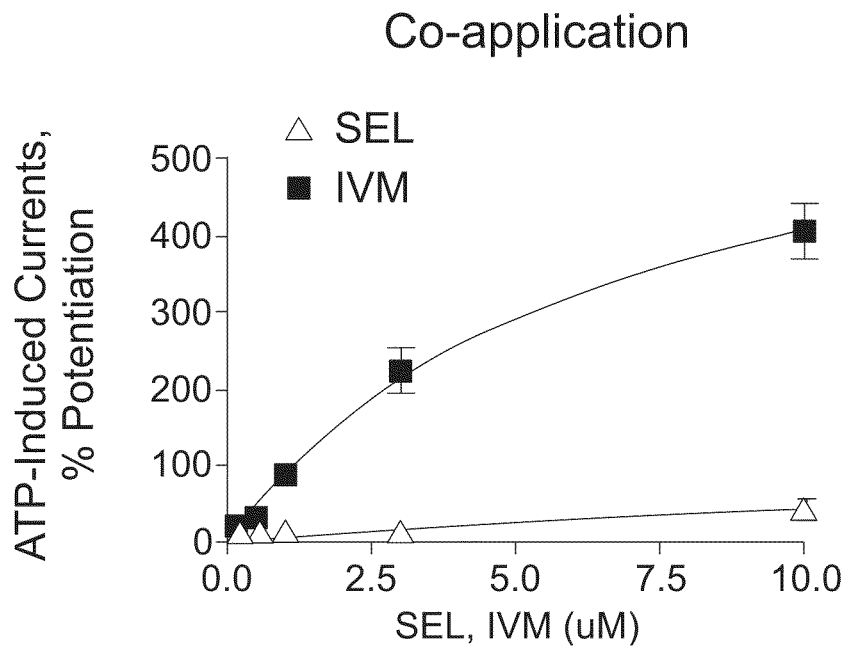
FIG. 10C provides plots of the percent potentiation for ATP-Induced currents versus AMB and SEL concentration (co-application)
Figure 10D:
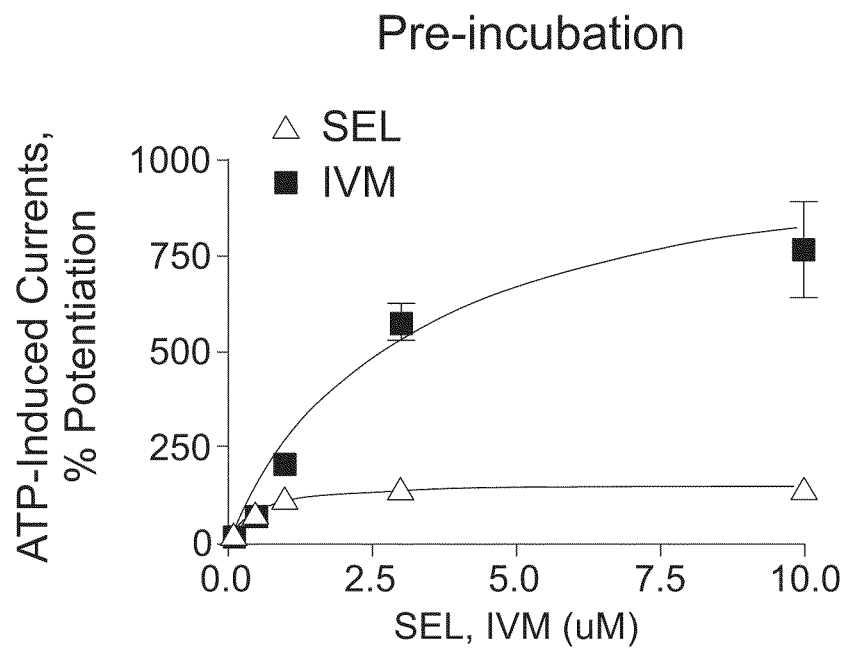
FIG. 10D provides plots of the percent potentiation for ATP-Induced currents versus AMB and SEL concentration (pre-incubation)

FIG. 10A provides a plot showing that at higher concentrations (≥3 µM) Abamectin (ABM) is dramatically more potent (3-10-fold) in modulating P2X4R activity than IVM. However, at lower concentrations (0.5 and 1.0 µM) as shown in FIG. 10B, ABM potentiates P2X4 activity to the same degree as IVM (Right panel). n=6-18. FIG. 10 indicates that in the case of IVM the potentiation is concentration dependent. FIGS. 10D and 10E provide plots showing that Selamectin (SEL) has substantially lower potency (3-5-fold) compared to IVM in modulating P2X4R activity. Significant potentiation of P2X4Rs observed only at 10 µM SEL during co-application (data not shown). *-$p<0.05$ compared to ATP only, n=4-10. As shown in FIGS. 10C and 10D there is small concentration-independent potentiation for SEL which is substantially weaker than IVM. There is higher potentiation with the pre-incubation protocol.

Figure 11A:
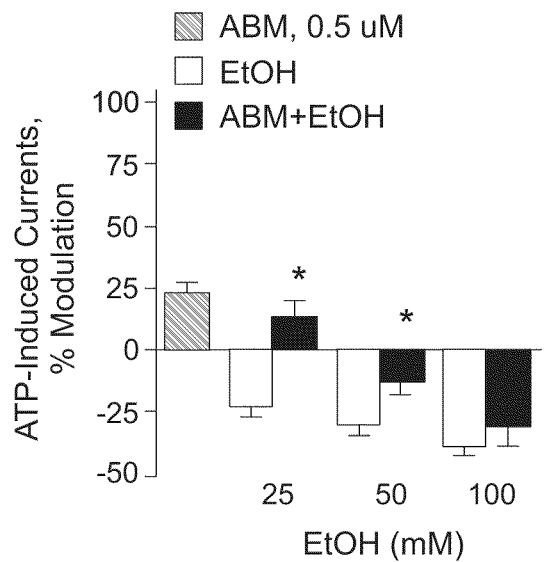
FIG. 11A provides a histogram of the percent modulation of ATP-Induced currents at various ethanol concentrations for AMB at 0.5 mM, ethanol, and ABM plus ethanol.
Figure 11B:
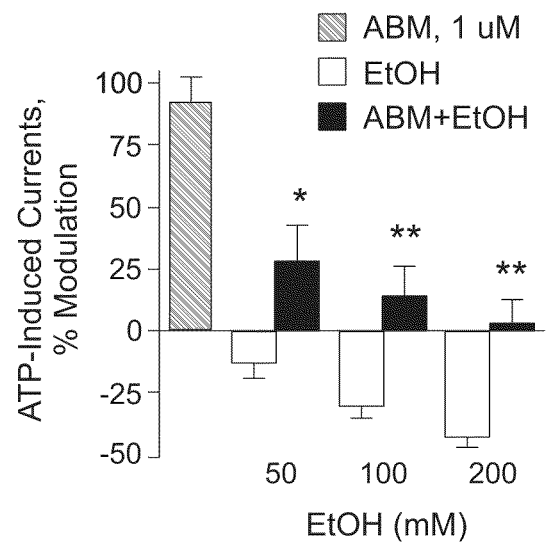
FIG. 11B provides a histogram of the percent modulation of ATP-Induced currents at various ethanol concentrations for AMB at 0.1 mM, ethanol, and ABM plus ethanol.
Figure 11C:
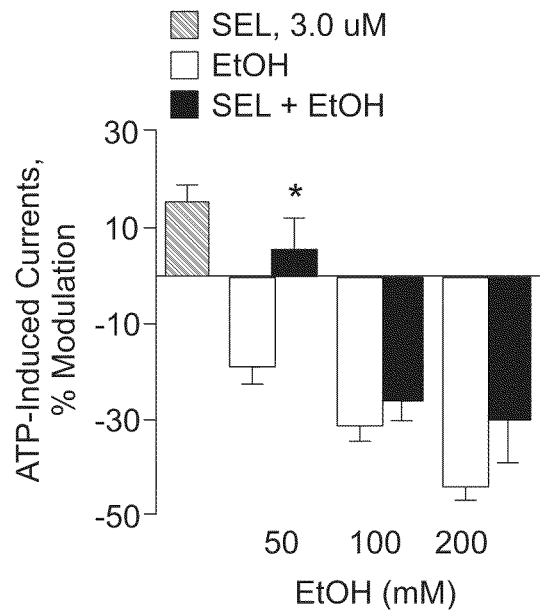
FIG. 11C provides a histogram of the percent modulation of ATP-Induced currents at various ethanol concentrations for SEL at 3 mM, ethanol, and SEL plus ethanol.
Figure 11D:
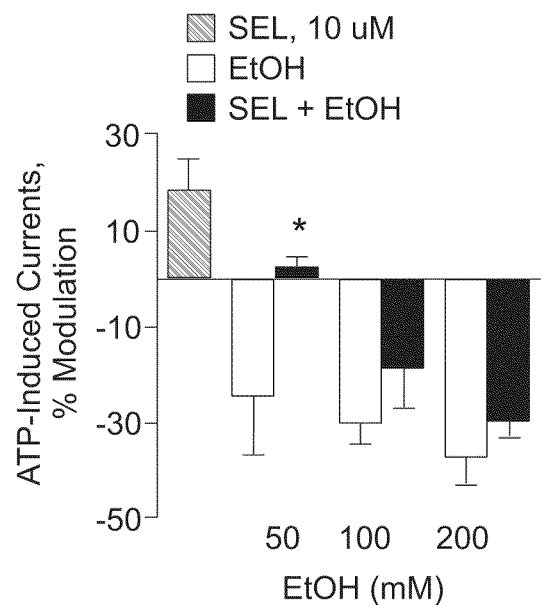
FIG. 11D provides a histogram of the percent modulation of ATP-Induced currents at various ethanol concentrations for SEL at 10 mM, ethanol, and SEL plus ethanol.

FIGS. 11A and 11B provide histograms showing that ABM antagonizes the inhibitory effects of ethanol when co-applied with ethanol. At 0.5 µM, ABM antagonizes the effects of 25 and 50 but not 100 mM ethanol (FIG. 11A), whereas at 1.0 µM ABM is able to antagonize ethanol at all the concentrations tested (FIG. 11B). *$P<0.05$, **$P<0.01$ compared to the ATP+50 mM ethanol, n=5-23. FIGS. 11C and 11D provide plots showing that during co-application with ethanol SEL at 3 and 10 mM has an antagonistic effect at 50 mM but not higher concentrations (100 and 200 mM) of ethanol. *$P<0.05$ compared to the ATP+50 mM ethanol, n=5-17. It should be noted that SEL has no effect on ethanol intake in mice.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

REFERENCES

1. Khakh, B. S. et al. International union of pharmacology. XXIV. Current status of the nomenclature and properties of P2X receptors and their subunits. *Pharmacol. Rev.* 53, 107-118 (2001).
2. Khakh, B. S. Molecular physiology of P2X receptors and ATP signalling at synapses. *Nat Reviews, Neurosci* 2, 165-174 (2001).
3. North, R. A. Molecular physiology of P2X receptors. *Physiol. Rev.* 82, 1013-1067 (2002).
4. Davies, D. L. et al. Effects of ethanol on adenosine 5'-triphosphate-gated purinergic and 5-hydroxytryptamine$_3$ receptors. *Alcohol Clin Exp Res* 30, 1-9 (2006).
5. Asatryan, L. et al. Roles of ectodomain and transmembrane regions in ethanol and agonist action in purinergic P2X2 and P2X3 receptors. *Neuropharmacology* 55, 835-843 (2008).
6. Popova, M. et al. A point mutation in the ectodomain-transmembrane 2 interface eliminates the inhibitory effects of ethanol in P2X4 receptors. *J Neurochem*. In press (2009).
7. Tabakoff, B. et al. Genetical genomic determinants of alcohol consumption in rats and humans. *BMC Biology*, In press (2009).

8. Rubio, M. E. & Soto, F. Distinct localization of P2X receptors at excitatory postsynaptic specializations. *J. Neurosci.* 21, 641-653 (2001).
9. Torres, G. E., Egan, T. M. & Voigt, M. M. Hetero-oligomeric assembly of P2X receptor subunits. Specificities exist with regard to possible partners. *J. Biol. Chem.* 274, 6653-6659 (1999).
10. Stoop, R. et al. Contribution of individual subunits to the multimeric $P2X_2$ receptor: Estimates based on methanethiosulfonate block at T336C. *Mol. Pharmacol.* 56, 973-981 (1999).
11. Jiang, L. H. et al. Subunit arrangement in P2X receptors. *J. Neurosci.* 23, 8903-8910 (2003).
12. Burnstock, G. Unresolved issues and controversies in purinergic signalling. *J Physiol* 586, 3307-3312 (2008).
13. Kawate, T., Michel, J. C., Birdsong, W. T. & Gouaux, E. Crystal structure of the ATP-gated P2X4 ion channel in the closed state. *Nature* 460, 592-598 (2009).
14. Li, M., Chang, T. H., Silberberg, S. D. & Swartz, K. J. Gating the pore of P2X receptor channels. *Nat Neurosci* 11, 883-887 (2008).
15. Burnstock, G. Introduction: P2 receptors. *Curr Top Med Chem* 4, 793-803 (2004).
16. Chizh, B. A. & Illes, P. P2X receptors and nociception. *Pharmacol. Rev.* 53, 553-568 (2001).
17. Xiong, K., Li, C. & Weight, F. F. Inhibition by ethanol of rat $P2X_4$ receptors expressed in *Xenopus* oocytes. *Br. J. Pharmacol.* 130, 1394-1398 (2000).
18. Davies, D. L., Machu, T. K., Guo, Y. & Alkana, R. L. Ethanol sensitivity in ATP-gated P2X receptors is subunit dependent. *Alcohol Clin Exp Res* 26, 773-778 (2002).
19. Davies, D. L. et al. Ethanol differentially affects ATP-gated P2X(3) and P2X(4) receptor subtypes expressed in *Xenopus* oocytes. *Neuropharmacology* 49, 243-253 (2005).
20. Geary, T. G. Ivermectin 20 years on: maturation of a wonder drug. *Trends in Parasitology* 21, 530-532 (2005).
21. Richard-Lenoble D., Chandenier J. & Gaxotte P. Ivermectin and filariasis. *Fundam Clin Pharmacol.* 17, 199-203 (2003).
22. Khakh, B. S., Proctor, W. R., Dunwiddie, T. V., Labarca, C. & Lester, H. A. Allosteric control of gating and kinetics at P2X4 receptor channels. *J Neuroscience* 19, 7289-7299 (1999).
23. Jelinkova, I. et al. Identification of P2X4 receptor-specific residues contributing to the Ivermectin effects on channel deactivation. *Biochem Biophys Res Commun.* 349, 619-625 (2006).
24. Silberberg, S. D., Li, M. & Swartz, K. J. Ivermectin interaction with transmembrane helices reveals widespread rearrangements during opening of P2X receptor channels. *Neuron* 54, 263-274 (2007).
25. Toulme, E., Soto, F., Garret, M. & Boue-Grabot, E. Functional properties of internalization-deficient P2X4 receptors reveal a novel mechanism of ligand-gated channel facilitation by Ivermectin. *Mol Pharmacol* 69, 576-587 (2006).
26. Bradley, R. J., Sterz, R. & Peper, K. The effects of alcohols and diols at the nicotinic acetylcholine receptor of the neuromuscular junction. *Brain Res* 295, 101-112 (1984).
27. Murrell, R. D., Braun, M. S. & Haydon, D. A. Actions of n-alcohols on nicotinic acetylcholine receptor channels in cultured rat myotubes. *J. Physiol.* 437, 431-448 (1991).
28. Wood, S. C., Forman, S. A. & Miller, K. W. Short chain and long chain alkanols have different sites of action on nicotinic acetylcholine receptor channels from *Torpedo*. *Mol. Pharmacol.* 39, 332-338 (1991).
29. Borghese, C. M., Ali, D. N., Bleck, V. & Harris, R. A. Acetylcholine and alcohol sensitivity of neuronal nicotinic acetylcholine receptors: mutations in transmembrane domains. *Alcohol. Clin. Exp. Res.* 26, 1764-1772 (2002).
30. Priel, A. & Silberberg, S. D. Mechanism of Ivermectin facilitation of human P2X4 receptor channels. *J. Gen. Physiol.* 123, 281-293 (2004).
31. Nemethy, G. & Scheraga, H. A. Strong interaction between disulfide derivatives and aromatic groups in peptides and proteins. *Biochem Biophys Res Commun* 98, 482-487 (1981).
32. Viguera, A. R. & Serrano, L. Side-chain interactions between sulfur-containing amino acids and phenylalanine in alpha-helices. *Biochemistry* 34, 8771-8779 (1995).
33. Bhattacharyya, R., Pal, D. & Chakrabarti, P. Disulfide bonds, their stereospecific environment and conservation in protein structures. *Protein Eng Des Sel* 17, 795-808 (2004).
34. Ma, B. & Nussinov, R. Trp/Met/Phe hot spots in protein-protein interactions: potential targets in drug design. *Curr Top Med Chem* 7, 999-1005 (2007).
35. Pless, S. A. et al. A Cation-{pi} Interaction in the binding site of the glycine receptor is mediated by a phenylalanine residue. *J. Neurosci.* 28, 10937-10942 (2008).
36. Grant, B. F. et al. The 12-month prevalence and trends in DSM-IV alcohol abuse and dependence: United States, 1991-1992 and 2001-2002. *Drug Alcohol Depend* 74, 223-234 (2004).
37. Harwood, H. J. Updating estimates of the economic costs of alcohol abuse in the United States: Estimates, update methods, and data. Report prepared by the Lewin Group from the National Institute on Alcohol Abuse and Alcoholism. 2000. Ref Type: Report
38. Heilig M. & Egli M. Pharmacological treatment of alcohol dependence: target symptoms and target mechanisms. *Pharmacol Ther.* 111, 855-876 (2006).
39. Steensland, P., Simms, J. A., Holgate, J., Richards, J. K. & Bartlett, S. E. Varenicline, an {alpha}4beta2 nicotinic acetylcholine receptor partial agonist, selectively decreases ethanol consumption and seeking. *Proc Natl Acad Sci USA* 104, 12518-12523 (2007).
40. Johnson, B. A. et al. Topiramate for treating alcohol dependence: A randomized controlled trial. *JAMA* 298, 1641-1651 (2007).
41. Perkins, D. I. et al. Loop 2 Structure in glycine and GABAA receptors plays a key role in determining ethanol sensitivity. *J. Biol. Chem.* 284, 27304-27314 (2009).

What is claimed is:

1. A method for reducing alcohol consumption in a subject, the method comprising:

identifying a subject exhibiting at least one symptom of alcoholism; and administering a therapeutically effective amount of an Ivermectin analogue-containing composition to the subject to reduce alcohol consumption wherein the composition is administered for a period of a week to several months, the Ivermectin analogue-containing composition comprising at least one Ivermectin analogue having the following formula:

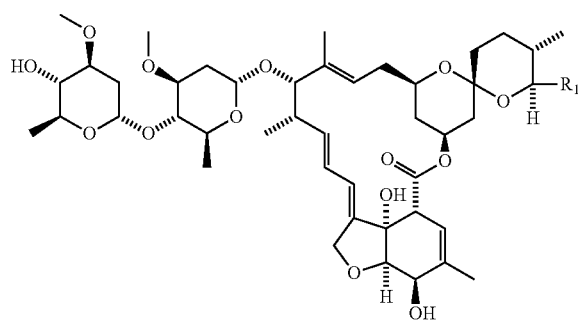

wherein $R_1$ is a $C_1$-$C_{10}$ alkyl.

2. The method of claim 1 wherein $R_1$ is methyl, ethyl, isopropyl, n-propyl, isobutyl, sec-butyl, or n-butyl.

3. The method of claim 1 wherein $R_1$ is isopropyl, n-propyl, isobutyl, or sec-butyl.

4. The method of claim 1 wherein the Ivermectin analogue-containing composition comprises Ivermectin.

5. The method of claim 1 wherein the Ivermectin analogue-containing composition is administered at a dose such that the Ivermectin analogue is delivered at a dose from about 0.025 to about 0.1 mg per kilogram of weight of the subject.

6. The method of claim 1 wherein the Ivermectin analogue-containing composition is administered at a dose of 2 to 8 mg per day.

7. The method of claim 1 further comprising monitoring in alcohol consumption by the subject.

8. The method of claim 1 wherein the Ivermectin analogue-containing composition is administered over a 24 hour period.

9. The method of claim 1 wherein the Ivermectin analogue-containing composition is administered on multiple days.

10. The method of claim 1 further comprising monitoring a reduction in alcohol consumption by the subject after administering of the Ivermectin analogue-containing composition.

11. The method of claim 1 wherein the Ivermectin analogue is administered for a period of 2 to 3 weeks.

12. A method for reducing alcohol consumption in a subject, the method comprising:
    identifying a subject exhibiting at least one symptom of alcoholism; and
    administering a therapeutically effective amount of Ivermectin to the subject to reduce alcohol consumption wherein the Ivermectin is administered for a period of a week to several months.

13. The method of claim 12 wherein the Ivermectin is delivered at a dose from about 1 to about 6.0 mg per kilogram of weight of the subject.

14. The method of claim 12 wherein the Ivermectin is delivered at a dose from about 1 to about 3 mg per kilogram of weight of the subject.

15. The method of claim 12 further comprising alcohol consumption by the subject.

16. The method of claim 12 wherein the Ivermectin analogue-containing composition is administered over a 24 hour period.

17. The method of claim 12 wherein the Ivermectin analogue-containing composition is administered on multiple days.

* * * * *